(12) United States Patent
Nicolosi

(10) Patent No.: US 6,197,004 B1
(45) Date of Patent: Mar. 6, 2001

(54) DEVICE FOR FIXING SUBCUTANEOUS CATHETERS

(76) Inventor: Adele Nicolosi, Via Barriere 7, Ferrara (IT)

( * ) Notice: Subject to any disclaimer, the term of this patent is extended or adjusted under 35 U.S.C. 154(b) by 0 days.

(21) Appl. No.: 09/339,461

(22) Filed: Jun. 24, 1999

(51) Int. Cl.[7] ..................................................... A61M 5/32
(52) U.S. Cl. ..................................... 604/175; 128/DIG. 26
(58) Field of Search ..................................... 604/174, 175, 604/177, 179; 128/DIG. 15, DIG. 26

(56) References Cited

U.S. PATENT DOCUMENTS 5,643,217 * 7/1997 Dobkin ............................. 604/174 X

* cited by examiner

*Primary Examiner*—Anh-Tuan T. Nguyen
(74) *Attorney, Agent, or Firm*—William J. Sapone; Coleman Sudol Sapone P.C.

(57) ABSTRACT

In a device for fixing subcutaneous catheters connected predominantly to a so-called open, or partially implantable system, in which a catheter is connected to a venous port, a peridural space, or other parts of a human body, the catheter is situated outside a subcutaneous pocket and introduced into a relative subcutaneous tunnel. The device includes a disc or a cylinder, which is introduced in said subcutaneous pocket and which features, made therein, at least three tubular through cavities, first, second and third, respectively. The three tubular cavities do not intersect. The catheter is introduced into the three tubular cavities.

6 Claims, 2 Drawing Sheets

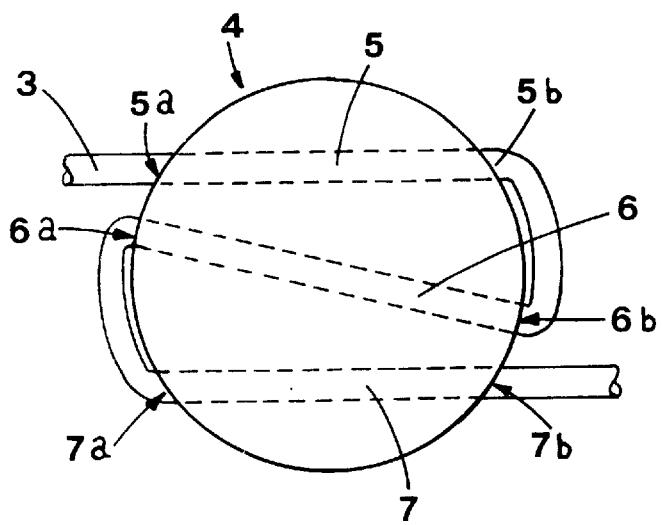
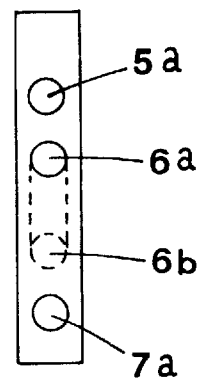
FIG. 1  FIG. 2
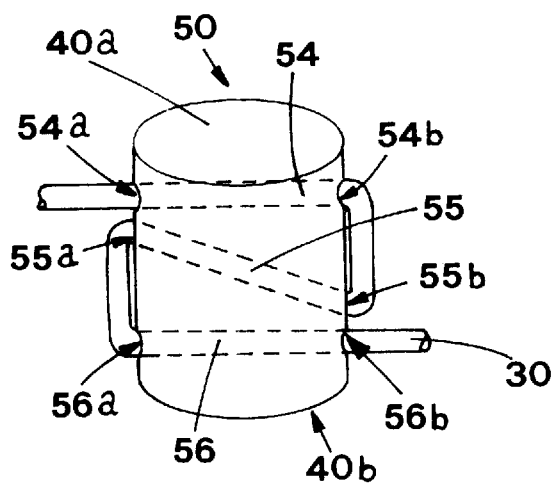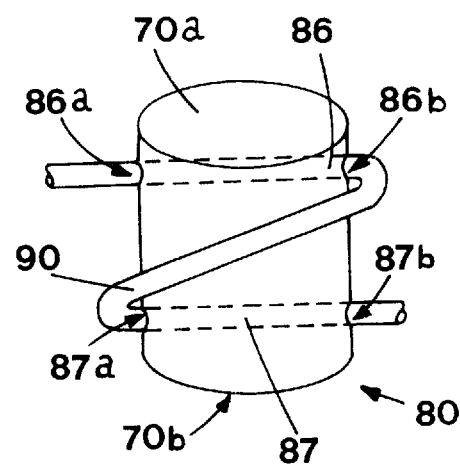
FIG. 3a  FIG. 3b
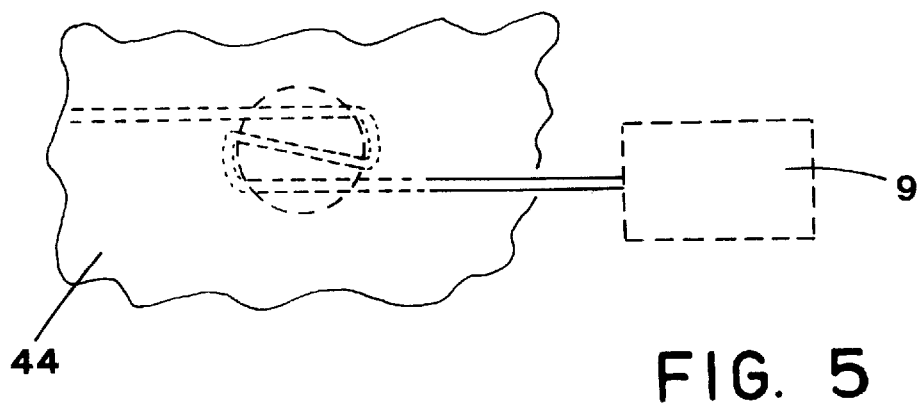
FIG. 5

DEVICE FOR FIXING SUBCUTANEOUS CATHETERS

FIELD OF THE INVENTION

The present invention relates to devices for fixing subcutaneous catheters.

DESCRIPTION OF THE PRIOR ART

Subcutaneous catheters must be implanted in the human body to be used for parenteral administering of medicines, liquids and nutritional solutions in specific regions, e.g. through the venous circle, peridural space, etc.

The catheters are indicated for patients who must undergo repeated blood samples taking, injections or prolonged infusion therapies.

If the catheters are implanted in one of the veins of the central venous systems or in the peridural space, it is necessary to implant the catheter distal end in the desired anatomic area.

Such implantation is obtained by the preparation of a subcutaneous pocket-like cut, a few centimeters long, made in the cutaneous or subcutaneous tissue.

Afterwards, a subcutaneous tunnel is prepared so as to allow the catheter to pass and be located and to set in communication the desired anatomic area and the subcutaneous pocket.

The catheter, properly introduced into the tunnel, goes out from the subcutaneous pocket.

It is possible to implant, in the subcutaneous pocket, a pump container, whose upper part is equipped with a feeding membrane which touches the skin.

The container is fed with medical substances by introducing needles into the skin in the membrane area.

The catheter is connected to the container by a corresponding connecting sleeve.

This type of implantation defines a closed or wholly implantable system.

According to another system, known as open or partially implantable system, the catheter is introduced in a subcutaneous tunnel and moved to the desired anatomic area.

The catheter of the subcutaneous pocket exits from the skin through another cutaneous hole, so as to be connected to an external infusion system.

With this system, the subcutaneous pocket is used to lock the catheter to a suitable device which fastens it, thus preventing it from detaching.

A first example of a fastening device is characterized in that a disc is introduced into the subcutaneous pocket.

A suitable adhesive is applied to the disc, so that the catheter can adhere thereto, thus eliminating or reducing to acceptable values, the catheter movement.

According to a second example, a material adhering to the catheter and to the subcutis is introduced to the portion of the catheter near the subcutaneous pocket.

Also in this case, the catheter is fastened and cannot be displaced.

A third example of fastening device is characterized by the use of another catheter, whose connecting end is equipped with a kind of pin coupling with a corresponding metallic connecting sleeve situated in the proximal end of the first catheter (or catheter to be fixed).

According to a fourth example, the fastening device is formed by two elements, the first of which is connectable to a sleeve and the second to a ring nut.

The catheter passes inside the two elements.

The ring nut is then screwed on the threading of the sleeve thus necking the sleeve and fastening the catheter inside the two elements.

The two just described systems have some drawbacks deriving from the devices for implantation and fastening the subcutaneous catheters.

In case of a close system of implantation and fastening, i.e. when the venous port is introduced in the subcutaneous pocket, the catheter can be displaced from the port, causing the system loss.

Before a medicine or a particular solution can be introduced to the membrane of the venous port, through a needle, the skin over the venous port must be disinfected; during this operation an infection of the area, where the catheter is placed, can occur.

Moreover, it is to be pointed out that this device is very expensive.

Also, the catheter implantation and fastening open system presents numerous disadvantages.

One of the most frequent disadvantages of the catheters implanted with the open system lies in the fact that the catheter moves very easily.

At present, this problem cannot be solved by any simple technical solution without complications and other difficulties.

If the catheter is fastened in the subcutaneous pocket by a disc with adhesive, an allergic reaction is possible.

Moreover, a possible unsticking can provoke a displacement of the catheter with respect to the disc, and consequently the loss of contact of the end of catheter with the anatomic region to be infused.

If the catheter is fastened in the subcutaneous pocket by introduction of the material adhering to the catheter as well as to the subcutis, the stick-in-place time is long, because the subcutis must produce fiber tissue which allows the introduced material to adhere to the pocket subcutis.

If the fastening device uses a second catheter, It can displace with respect to the catheter to be fastened, which results in medicine leakage to the pocket while the desired point or area is not reached by this substance.

The displacement occurs because of the detachment of the plug-in pin corresponding to the end of the second catheter from the connecting sleeve of the catheter to be fastened.

Moreover, a fastening device using a second catheter is expensive, due to high manufacturing costs of the plug-in pin implanted in the second catheter and of the connecting sleeve implanted in the first catheter.

The fastening device formed by the sleeve and ring nut is expensive, complicated and easy to wear and tear.

SUMMARY OF THE INVENTION

The present invention has been evolved with the main object to propose a device for fixing catheters which overcomes the above mentioned disadvantages and which is easy to be implanted.

Another object of the present invention is to propose a system which carries out a simple, cheap, extremely functional and reliable technical solution.

The above mentioned objects are obtained, in accordance with the contents of claims, by means of a device for fixing subcutaneous catheters connected to an open, or partially implantable system, in which a catheter is connected to a venous port, a peridural space, or other parts of a human body, and is situated outside a subcutaneous pocket and introduced into a relative subcutaneous tunnel, wherein the device t includes a member which is introduced in said subcutaneous pocket and which features, made therein, at least three tubular through cavities, first, second and third, respectively, not intersecting each other, with said catheter introduced into said tubular through cavities.

According to another embodiment, the member which is introduced in said subcutaneous pocket, features, made therein, two tubular through cavities.

According to another embodiment, the member is a disc and the tubular cavities define relative entrance and exit holes along a circumference of said disc.

Another embodiment is disclosed in which the member is a cylinder of anallergic material and the tubular cavities define entrance and exit holes along an extension of said cylinder.

BRIEF DESCRIPTION OF THE CLAIMS

The characteristic features of the invention will become apparent from the following description with reference to the enclosed drawings, in which:

FIG. 1 is a front view of the device for fixing subcutaneous catheters;

FIG. 2 is a lateral view of the same device with inflow/outflow holes, which have been pointed out;

FIG. 3a is a lateral view of an embodiment of the proposed device;

FIG. 3b is a lateral view of another embodiment of the proposed device;

FIG. 5 is a front view of the device for fixing catheters, pointing out the connection between the catheter and a venous port.

DESCRIPTION OF THE PREFERRED EMBODIMENTS

Figure 4:
FIG. 4 shows an example of the collocation of the device.

With reference to the above mentioned figures, the reference numeral 4 generally designates the device for fixing subcutaneous catheters in the so-called open systems, while reference numeral 3 indicates a subcutaneous catheter and the reference numeral 9 a venous port.

The device 4 includes a disc with three tubular through cavities 5, 6, 7 made therein, namely a first, a second and a third cavity respectively, which define holes 5a, 6b, 7a through which the catheter enters and holes 5b, 6a, 7b through which the catheter exits.

The tubular cavities are arranged in such a way as to not intersect each other.

The entrance and exit holes are situated on the circumference of the disc 4; the holes 5a, 5b are connected by the first cavity 5, which, in the shown example, is parallel to the disc reference diameter.

The holes 7a, 7b are connected by the third cavity 7, which is likewise parallel to the disc reference diameter.

The holes 6a, 6b are connected by the second cavity 6, situated, in the shown example, inside the disc, along a slanted axis.

In order to be fixed to the device 4, the catheter 3, going out of the subcutaneous tunnel, must be introduced into the entrance hole 5a.

The catheter passes through the first cavity 5 and goes out through the hole 5b; afterwards, the catheter is introduced into the remaining holes first into 6b, then 6a, later 7a and finally into 7b.

The so arranged catheter forms a serpentine inside the device 4.

The proximal end of the catheter 3 will be connected later to the venous port 9.

The device with the catheter implanted is introduced into a subcutaneous pocket 44, whose dimensions are proportional to the dimensions of the device.

The so blocked catheter exits from the subcutaneous pocket through a subcutaneous tunnel, so as to connected to the venous port 9.

The connection of the catheter to the venous port has not been shown, since its technique is known for subcutaneous catheters in open systems.

FIG. 3a shows a possible embodiment of the device for fixing subcutaneous catheters.

According to this embodiment, a fixing device 50 includes a small cylinder, which features made therein entrance holes 54a, 55b, 56a and exit holes 54b, 55a, 56b.

The holes are connected by three tubular through cavities 54, 55, 56, first, second and third, respectively, through which a subcutaneous catheter 30 passes.

Moreover, the tubular cavities are arranged in such a way, as not to intersect each other.

As seen in FIG. 3a, the cavities 54, 56 are parallel to the bases 40a, 40b of the cylinder 50, while the cavity 55 is situated between the first and second ones along a slanting axis.

The catheter 30 is introduced into suitable holes in the same way as described for the device 4, following this order:

firstly, the catheter enters through the hole 54a, then it exits through the hole 54b; afterwards, the catheter enters the hole 55b and exits through the hole 55a; lastly the catheter enters the hole 56a and exits through the hole 56b.

The cylinder 50 is introduced into a subcutaneous pocket, whose dimensions are proportional to the dimensions of the cylinder 50.

FIG. 3b shows another embodiment of the device for fixing subcutaneous catheters.

According to this embodiment, a fixing device 80 includes a cylinder, which features made therein entrance holes 86a, 87a and exit holes 86b, 87b.

The holes are connected by two tubular through cavities 86, 87 first and second, respectively, through which a subcutaneous catheter 90 passes.

Moreover, the tubular cavities are arranged in such a way, as not to intersect each other and to be parallel to the bases 70a, 70b of the cylinder 80.

The catheter 90 is introduced into the suitable holes following this order: it enters the hole 86a, then exits from the hole 86b, the enters the hole 87a and exits from the hole 87b.

According to this solution, after exiting the hole 86b, the catheter 90 passes outside the cylinder and enters it again through the hole 87a.

The cylinder 80 is introduced into a subcutaneous pocket, whose dimensions are proportional to the dimensions of the cylinder.

One of the advantages of the described device for fixing subcutaneous catheters derives from the fact that it is easy to manufacture, does not use movable parts for fixing the catheter and definitely prevents the catheter from displacement.

Another advantage of the proposed device results from the fact that it does not use adhesives to make the catheter adhere to the subcutaneous pocket, therefore allergic reactions to adhesive agent are eliminated and the catheter is prevented from displacement due to the loss of the adhesive adherence.

A further advantage of the proposed device for fixing subcutaneous catheters lies in the fact that it does not feature movable parts, parts which are easy to wear and tear, or sharp parts, which could cut the catheter during the implantation.

Yet further advantage of the proposed device results from the use of tubular cavities, which allow the catheter 4 to be arranged inside the device 4 like a serpentine; in this way the catheter seems embedded inside the cavities, which prevents it from displacements even in cases of pulling because of the patient's particular movements.

In order to displace the catheter, a doctor must do it deliberately and manually.

Finally, device manufacturing is cheap because of its simplicity.

It is understood that what above has been described as a mere, non limitative example, therefore possible constructive variants of the proposed device remain within the protective scope of the present technical solution, as described above and claimed hereinafter.

What is claimed is:

1. A device for fixing a subcutaneous catheter comprising:
    a catheter locatable within a subcutaneous tunnel; and,
    a fixing member locatable within a subcutaneous pocket, the fixing member having a serpentine cavity therein, the catheter having a portion residing within the cavity in a serpentine pattern so as to limit movement of the catheter.

2. The device of claim 1, wherein the fixing member is a disc, said tubular through cavities having entrances and exits along a circumference of the disc.

3. The device of claim 1, wherein the fixing member is a cylinder.

4. The device of claim 1, wherein the fixing member is made of anallergic material.

5. The device of fixing a subcutaneous catheter comprising:
    a catheter locatable within a subcutaneous tunnel; and,
    a fixing member locatable within a subcutaneous pocket, the fixing member having at least two tubular through cavities therein, the catheter having a portion residing within the at least two tubular cavities in a serpentine pattern so as to limit movement of the catheter.

6. The device of claim 5, wherein the fixing member has three tubular through cavities.

* * * * *